(12) United States Patent
Nurnberg

(10) Patent No.: US 10,792,225 B1
(45) Date of Patent: Oct. 6, 2020

(54) SECURE MEDICATION DISPENSER

(71) Applicant: David Nurnberg, Colorado Springs, CO (US)

(72) Inventor: David Nurnberg, Colorado Springs, CO (US)

( * ) Notice: Subject to any disclaimer, the term of this patent is extended or adjusted under 35 U.S.C. 154(b) by 39 days.

(21) Appl. No.: 16/268,917

(22) Filed: Feb. 6, 2019

(51) Int. Cl.
*A61J 7/04* (2006.01)
*G07F 17/00* (2006.01)
*G16H 20/13* (2018.01)

(52) U.S. Cl.
CPC ........ *A61J 7/0454* (2015.05); *G07F 17/0092* (2013.01); *G16H 20/13* (2018.01)

(58) Field of Classification Search
CPC ....... G16H 20/13; A24F 15/005; A24F 15/10; A24F 15/04
USPC .......................................................... 221/14
See application file for complete search history.

(56) References Cited

U.S. PATENT DOCUMENTS

| | | | | |
|---|---|---|---|---|
| 2,179,716 A * | 11/1939 | Eiler | ........................ | A24F 15/10 221/147 |
| 2,741,109 A * | 4/1956 | Dupuis | .................... | A24F 15/18 431/319 |
| 2,815,814 A * | 12/1957 | Taylor | ...................... | B26D 7/18 83/139 |
| 3,815,780 A * | 6/1974 | Bauer | ..................... | G04C 21/36 968/603 |
| 5,971,205 A * | 10/1999 | Michaels | ................ | G07F 9/105 221/135 |
| 6,125,082 A * | 9/2000 | Reid | ...................... | A24F 15/005 131/270 |
| D522,691 S * | 6/2006 | Willis | ......................... | D27/184 |
| 7,359,765 B2 * | 4/2008 | Varvarelis | ............. | A61J 7/0481 700/237 |
| 10,157,265 B1 * | 12/2018 | Darnell | ................... | G16H 20/13 |
| 2016/0227970 A1 * | 8/2016 | Diamond | ........... | B65H 35/0086 |
| 2019/0031441 A1 * | 1/2019 | Jin | .......................... | G07F 11/46 |
| 2019/0070075 A1 * | 3/2019 | Hamilton | .............. | A61J 7/0481 |

* cited by examiner

*Primary Examiner* — Timothy R Waggoner
(74) *Attorney, Agent, or Firm* — Sanchelima & Associates, P.A.; Christian Sanchelima; Jesus Sanchelima

(57) ABSTRACT

The present invention is disclosing a secure medication dispenser. Secure medication dispenser comprises a housing. Housing comprise a timer configured to set time to release a specified dosage of each of a plurality of medications. Housing further comprises an environment control system configured to control one or more physical environmental characteristic for said plurality of medications inside said housing to preserve corresponding potencies. Housing further comprises a plurality of authorization mechanisms configured to lock and seal said plurality of medications inside said housing. Housing further comprises an electronic dispensing system configured to dispense, at a time, a single medication from corresponding plurality of medications to a user upon receiving an ejection command and successful authorization of said user by the plurality of authorization mechanisms.

10 Claims, 5 Drawing Sheets

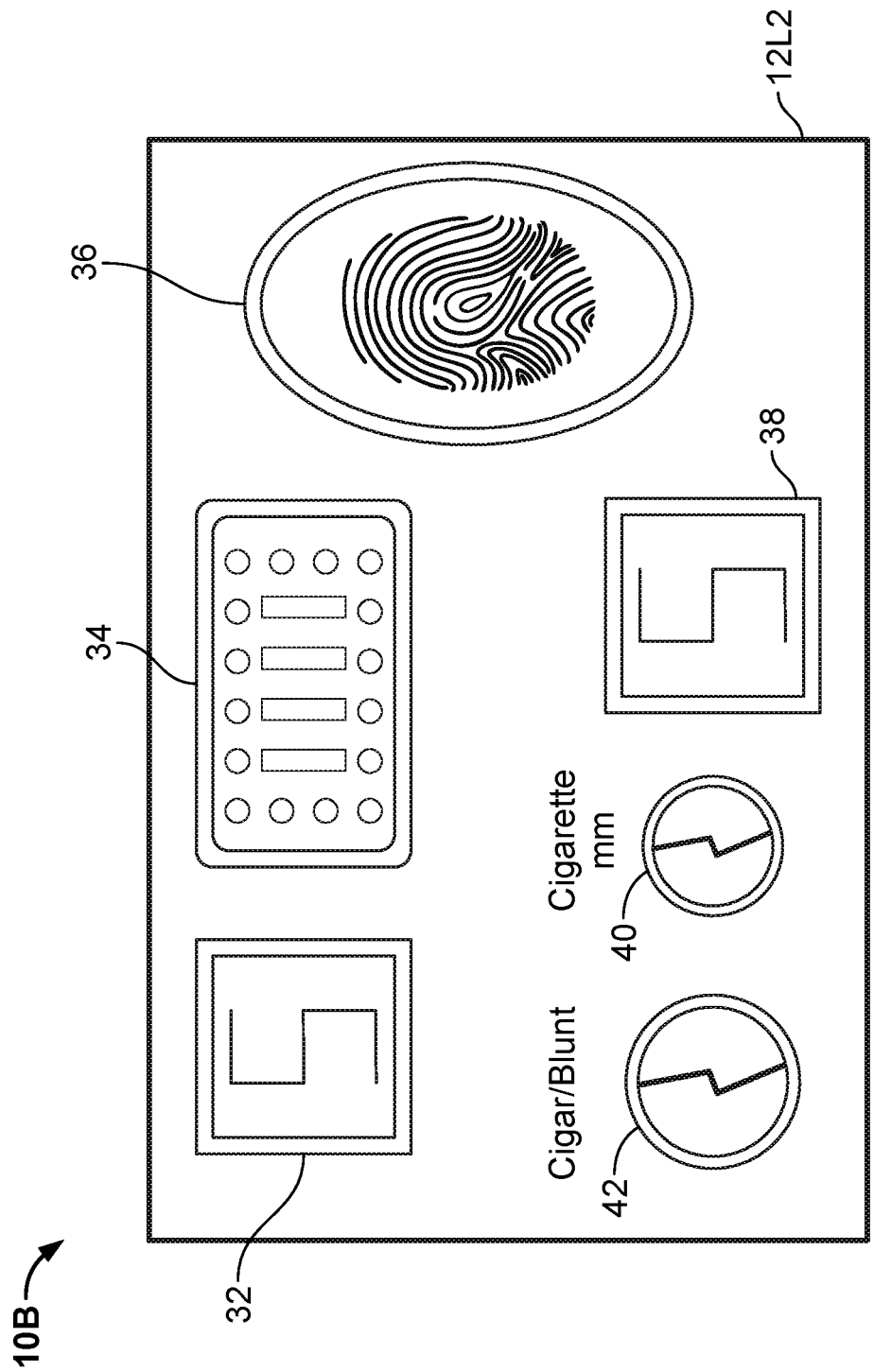

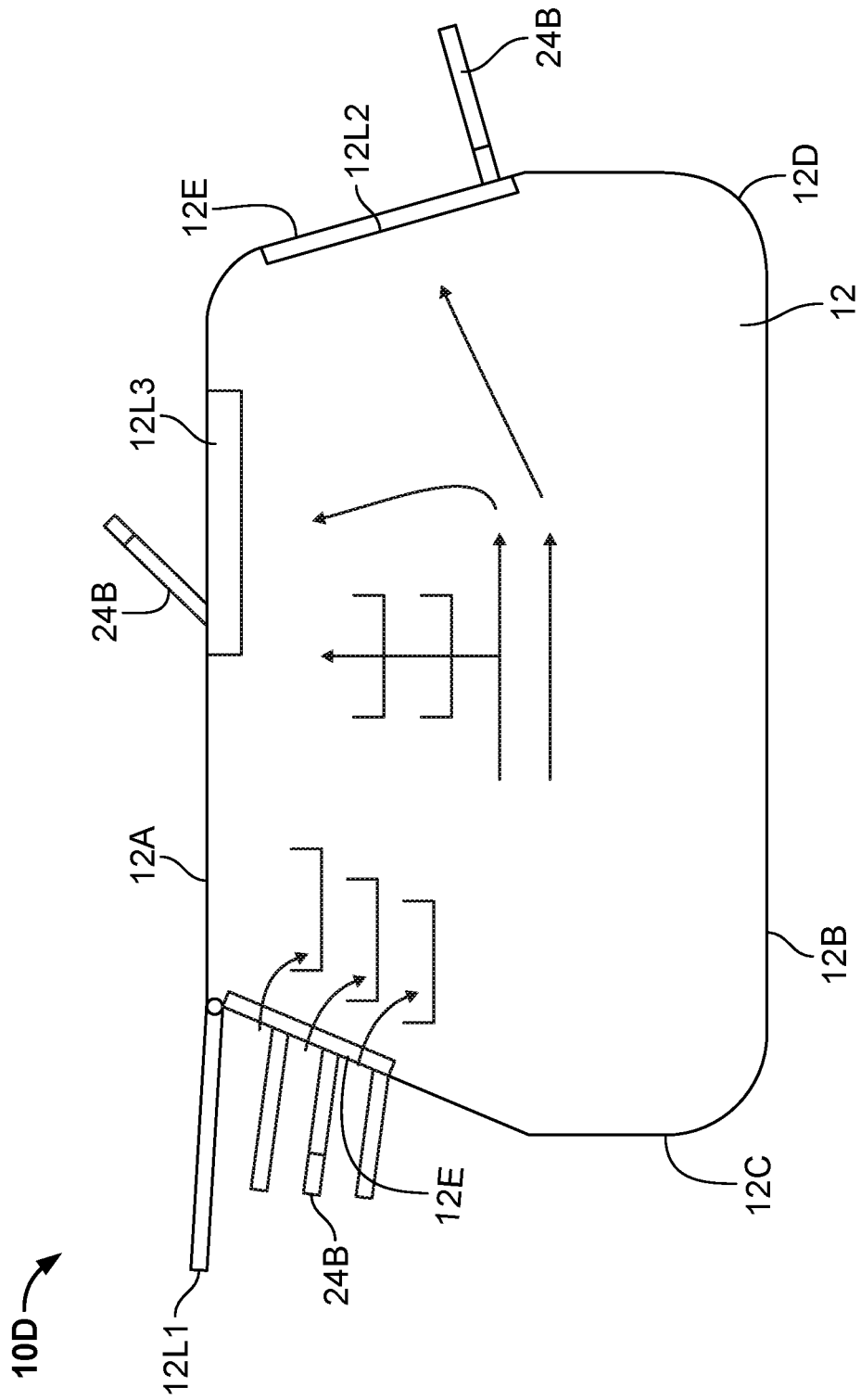

SECURE MEDICATION DISPENSER

BACKGROUND OF THE INVENTION

1. Field of the Invention

The present disclosure relates to a secure medication dispenser. More particularly, the present disclosure relates to a secure medication dispenser that assures proper dosing and prevents theft and abuse of prescription medications.

2. Description of the Related Art

Patients are supposed to have timely dosage of prescribed medication. It becomes utmost important to avoid overdosage of such medications and at the same time, prevent theft and abuse of prescription medications.

Several designs of dispensers have been presented in the past. None of them, however, presents a simple and secure dispenser that is user friendly, reliable, and prone to theft and abuse by users other than the owner.

Applicant believes that a related reference corresponds to U.S. Pat. No. 7,359,765 filed by Nicholas M. Varvarelis that discloses an electronic pill dispenser which includes a container and a cap removably attached to the container. Components of the pill dispenser include a power source, pill dispenser circuitry, a real time clock, a counter, a display, a dispensing mechanism, a sensor, a visual indicator, an audible indicator, an input/output interface, an input output port, and a communication bus electrically interconnecting the components. However, such electronic pill dispenser is limited in functionality and inconvenient to use.

Other documents describing the closest subject matter provide for a number of more or less complicated features that fail to solve the problem in an efficient and economical way. None of these patents suggest the novel features of the present invention.

SUMMARY OF THE INVENTION

It is an object of the present invention to provide a secure medication dispenser. Secure medication dispenser comprises a housing. Housing comprise a timer configured to set time to release a specified dosage of each of a plurality of medications. Housing further comprises an environment control system configured to control one or more physical environmental characteristic for said plurality of medications inside said housing to preserve corresponding potencies. Housing further comprises a plurality of authorization mechanisms configured to lock and seal said plurality of medications inside said housing. Housing further comprises an electronic dispensing system configured to dispense, at a time, a single medication from corresponding plurality of medications to a user upon receiving an ejection command and successful authorization of said user by the plurality of authorization mechanisms. In accordance with an embodiment, environment control system comprises a humidifier and a temperature controller configured to control humidity and temperature inside said housing.

In accordance with an embodiment, housing further comprising nylon fastener strips or suction cups configured to be mounted on bottom surface of said housing of said secure medication dispenser, and an LED light system configured to indicate low supply of one or more of said plurality of medications.

In accordance with an embodiment, housing may further comprise a top plate, a face plate, and a rear plate. Top plate may conceal a lighter and/or a matchstick, said top plate being configured to be opened or closed by a pushing and releasing mechanism. Face plate may be angled upward. Face plate may be configured to accommodate said plurality of authorization mechanisms and said electronic dispensing system. Rear plate may be angled upward and may be configured to accommodate a loading mechanism for said plurality of medications. Housing may further comprise a plurality of trays configured to accommodate said plurality of medications of different sizes.

In accordance with various embodiments, plurality of medications may comprise two or more of a cigarette, a cigar, a joint, an mm medication, and a blunt. Physical environmental characteristic may correspond to a humidity level inside said housing. Plurality of authorization mechanisms may comprise two or more of a fingerprint recognition device, an authorized key, and a voice recognition device. User may be a patient suffering from Alzheimer, Dementia, Chronic pain, Epilepsy, Cognitive Dysfunction, Memory loss, or other such ailment. Secure medication dispenser may be waterproof, shatterproof, overdose proof, and theft proof. Secure medication dispenser may be one of a variable shape, a square shape, a rounded shape, a horseshoe shape, or a combination thereof Further objects of the invention will be brought out in the following part of the specification, wherein detailed description is for the purpose of fully disclosing the invention without placing any limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 1A represents a face plate of secure medication dispenser 12 of present invention in its front view 10B, according to an embodiment described herein.

FIG. 1C represents secure medication dispenser 12 of present invention in its second side view 10D, according to an embodiment described herein.

DETAILED DESCRIPTION OF THE EMBODIMENTS OF THE INVENTION

Figure 1:
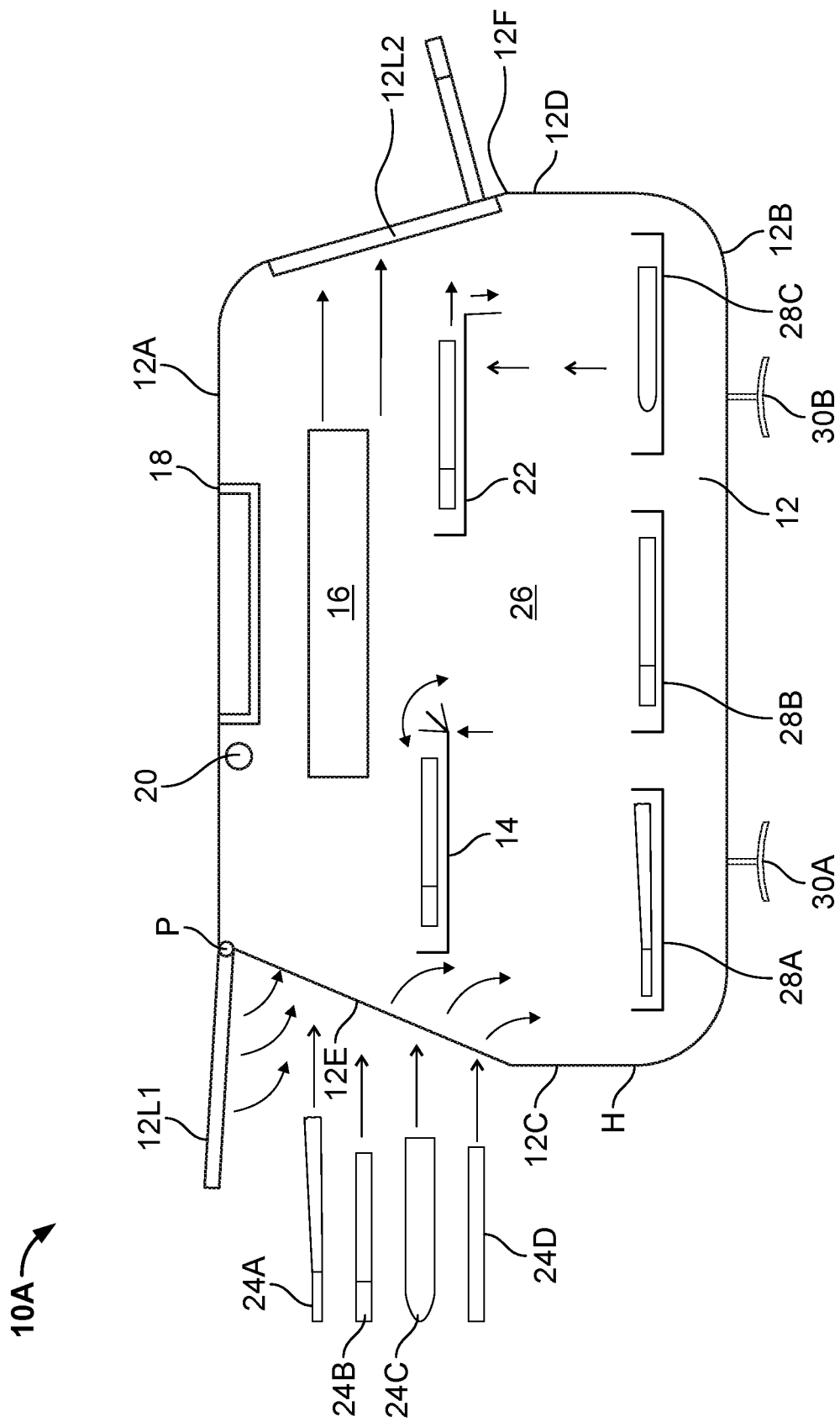
FIG. 1 represents a secure medication dispenser 12 of present invention in its first side view 10A, according to an embodiment described herein.

Referring now to the drawings, FIGS. 1-1D, where the present invention is generally referred to with numeral 12, it can be observed that a secure medication dispenser, in accordance with one embodiment, is provided that includes various components, a described hereinafter.

Figure 1B:
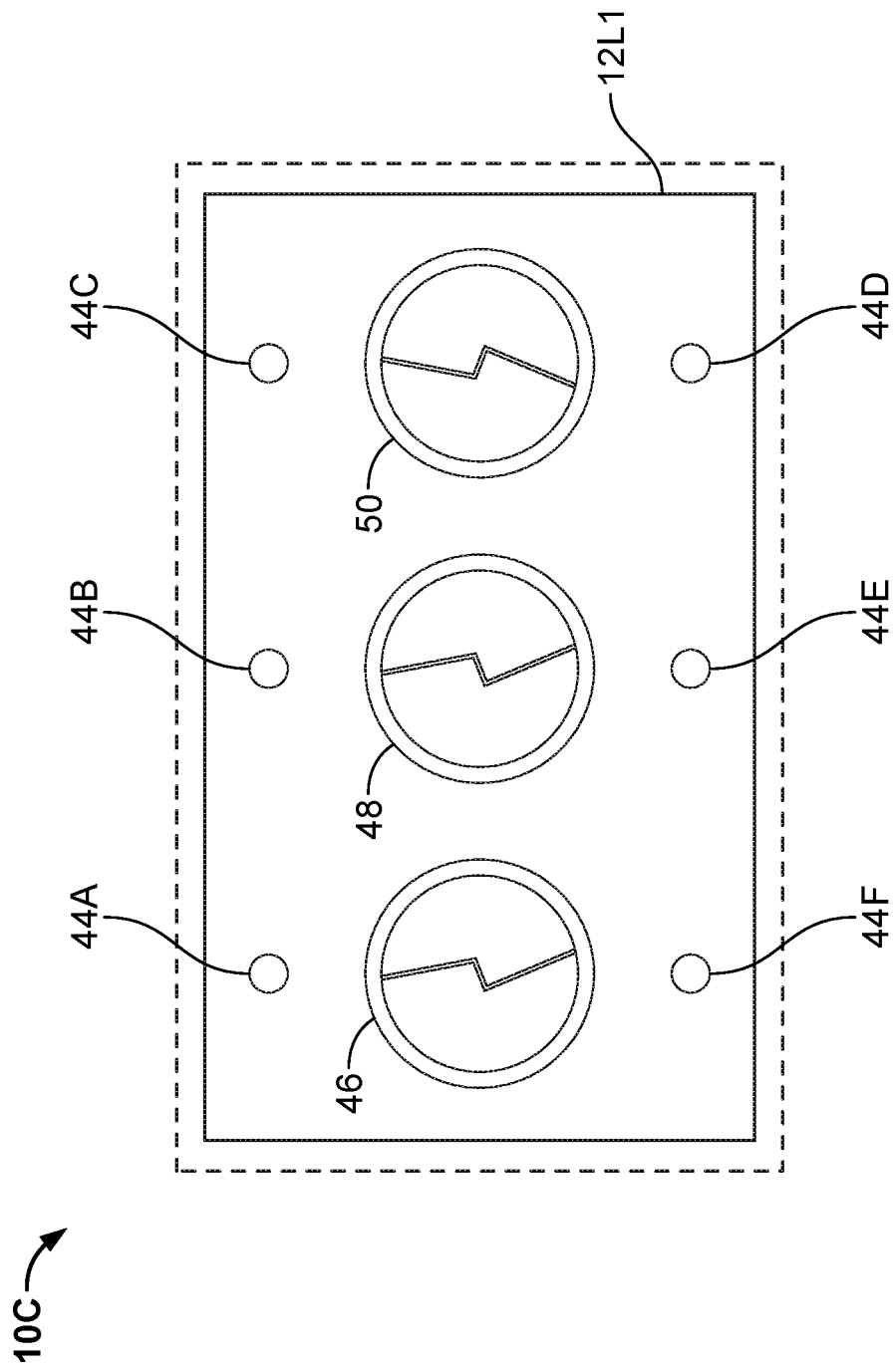
FIG. 1B represents a rear plate of secure medication dispenser 12 of present invention in its rear view 10C, according to an embodiment described herein.

FIG. 1 represents a secure medication dispenser 12 of present invention in its first side view 10A; FIG. 1A represents a face plate of secure medication dispenser 12 of present invention in its front view 10B; FIG. 1B represents a rear plate of secure medication dispenser 12 of present invention in its rear view 10C; FIG. 1C represents secure medication dispenser 12 of present invention in its second side view 10D, according to an embodiment described herein; and FIG. 1D represents secure medication dispenser 12 of present invention in its front and rear views 10E1 and 10E2, respectively, according to an embodiment described herein. Secure medication dispenser 12 may be waterproof, shatterproof, overdose proof, and theft proof. Shape of secure medication dispenser 12 may be one of a variable shape, a square shape, a rounded shape, a horseshoe shape, or a combination thereof.

FIG. 1 illustrates secure medication dispenser 12 in its first side view 10A. In first side view 10A, there is shown a housing 26 with a shorter top edge 12A and a longer bottom edge 12B, parallel to each other. There is further shown a left-side edge 12C and a right-side edge 12D of housing 26, parallel to each other, but extending upto half of actual height of secure medication dispenser 12. From thereon, left-side slanting edge 12E and right-side slanting edge 12F, slanting inwards, extend to meet shorter top edge 12A at either ends, respectively.

Left-side edge slanting 12E engages with rear plate 12L1 acting as an opening and closing lid about a pivot P. Right-side edge 12F abuts with face plate 12L2 configured to accommodate a plurality of authorization mechanisms and an electronic dispensing system, described in detail in FIG. 1A.

Within housing 26, there are shown a plurality of receiving trays 14, configured to receive a plurality of medications of different sizes, such as an mm joint 24A (size of 6-8"), a cigarette 24B (size of 6-8"), a cigar 24C (size of 10-12") or (17"-18"), and an mm blunt 24D (size of 10-12"). Rear plate and loading of plurality of medications are described in FIG. 1B.

Once loaded, humidifier 16 may be configured to control a physical environmental characteristic, such as humidity, for plurality of medications inside housing 26 to preserve corresponding potencies and freshness. In accordance with an embodiment, a temperature control system (not shown) may be configured to control another physical environmental characteristic, such as temperature, for plurality of medications inside housing 26 to preserve corresponding potencies and freshness.

Towards top edge 12A, there is shown a recessed handle 18 with corresponding push button 20 that may be manipulated to rise up handle 18, when user desires to carry secure medication dispenser 12. User may be a patient suffering from Alzheimer, Dementia, Chronic pain, Epilepsy, Cognitive Dysfunction, Memory loss, or other such ailment.

Before ejection of at least one of plurality of medications, storage of housing 26 may be configured to store plurality of medications under controlled environmental conditions, as discussed above. Vertical edge on one side of one of plurality of receiving trays 14 flips down and plurality of receiving trays 14 cycles down in storage area 16 as trays, such as 28A, 28B, and 28C. For example, mm joint 24A may be cycled down in tray 28A, cigarette 24B may be cycled down in tray 28B, and cigar 24C may be cycled down in tray 28C. One of trays 28A, 28B, or 28C, in accordance with receiving ejection command and user authentication via at least one of plurality of authentication mechanisms, may be raised or cycled up till face plate 12L2, as indicated by tray position 22. From corresponding dispensing point located on face plate 12L2 or top plate 12L3, one of plurality of medications, at a time, is ejected for user. As observed in FIG. 1A, the face plate includes dispensing points 42 and 40 which are adapted to dispense the plurality of said medications. FIG. 1C depicts the plurality of medications being dispensed.

Towards bottom edge of housing 26 of secure medication dispenser 12, there are shown retractable suction cups 30A and 30B configured to be mounted on bottom surface of housing 26 of secure medication dispenser 12. Alternatively, there may be nylon fastener strips or Velcro installed at bottom surface of housing 26 of secure medication dispenser 12.

Referring to FIG. 1A, there is shown face plate 12L2 angled upward and configured to accommodate an LED light system 32, plurality of authorization mechanisms, such as voice recognition system 34 and fingerprint recognition system 36, and electronic dispensing system, such as dispensing points 40 and 42. In accordance with an embodiment, plurality of authorization mechanisms may be configured to lock and seal plurality of medications inside housing 26. Electronic dispensing system may be configured to dispense, at a time, a single medication from corresponding plurality of medications to a user upon authorization by plurality of authorization mechanisms.

Fingerprint recognition system 36 may be installed towards right (for right handed user) or left side (for left handed user) of face plate 12L2. Face plate 12L2 may further accommodate a timer 38 configured to set time to release a specified dosage of each of plurality of medications. Timer 38 may render audio, visual, or audio-visual feedback to user about time to take one or more of plurality of medications as prescribed. LED light system 32, such as LED supply indicator, may be configured to indicate low supply of one or more of plurality of medications. Dispensing points 40 (for example for cigarette and medical marijuana (mm)) and 42 (for example for cigar or blunt) may be holes having rubber flanges to hold medication without use of hands. It may be helpful for users without ability to hold, for example amputees or trained dogs).

Referring to FIG. 1B, there is shown rear plate 12L1 angled upward and configured to accommodate loading mechanism for plurality of medications. There are shown a plurality of buttons 44A to 44F. There are further shown a plurality of loading points, for example a first loading point 46 for loading mm joint 24A, operated by buttons 44A and 44F, a second loading point 48 for loading cigarette 24B and joint, operated by buttons 44B and 44E, respectively, and a third loading point 50 for loading cigar 24C and blunt, operated by buttons 44C and 44D, respectively. Buttons 44A to 44F may be manipulated to notify secure medication dispenser 12 about which medication is being loaded and which receiving tray should secure medication dispenser 12 be used.

Referring to FIG. 1C, there is shown second side view 10D of housing 26 of secure medication dispenser 12. In addition to top edge 12A, bottom edge 12B, left and right side edges 12C and 12D respectively, a left and right side slanting edges 12E and 12F respectively, there is further shown a top plate 12L3. Top plate 12L3 may conceal a lighter and/or a matchstick and may be configured to be opened or closed by a pushing and releasing mechanism. As illustrated, for example, cigarette 24B once loaded may be ejected upon receiving an ejection command and successful authorization of user. Ejection may be through face plate 12L2 in a slanting direction or through top plate 12L3 in a vertical direction.

Figure 1D:
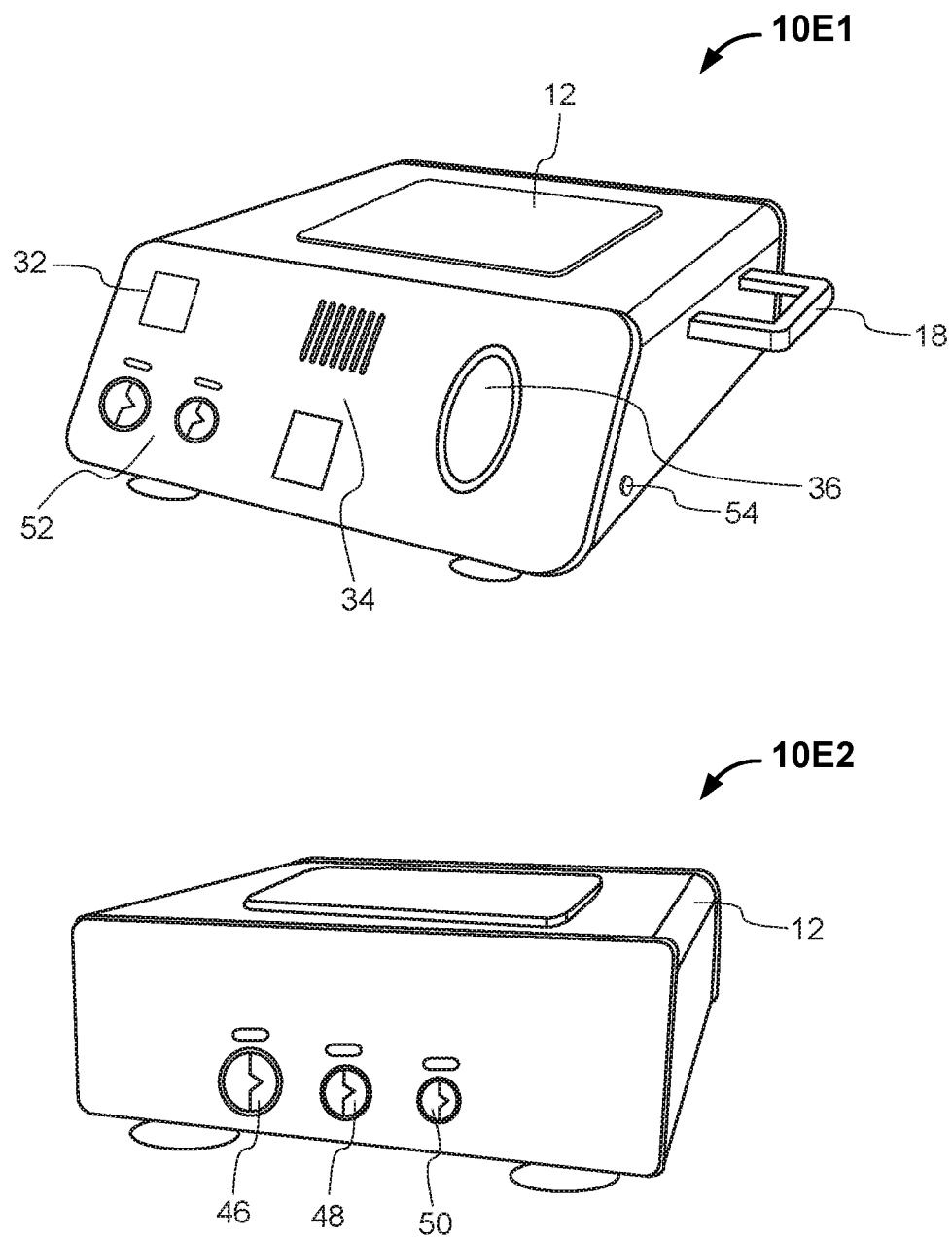
FIG. 1D represents secure medication dispenser 12 of present invention in its front and rear views 10E1 and 10E2, respectively, according to an embodiment described herein.

Referring to FIG. 1D, there are shown front and rear views 10E1 and 10E2, respectively, of secure medication dispenser 12. In addition to the various electronic systems described above, for example, the recessed handle 18 (which is illustrated to be towards one side of secure medication dispenser 12), LED light system 32 (for indicating number of units remaining), voice recognition system 34, and fingerprint recognition system 36, there are further shown dispenser slots 52 that correspond to dispensing points, and a suction cup button 54.

Referring to FIGS. 1-1D, various electronic systems, for example, timer 38, environment control system, such as humidifier 16 and temperature controller, plurality of authorization mechanisms, and electronic dispensing system, in housing 26 of secure medication dispenser 12 may be provided power supply by a rechargeable battery (not shown) or solar power panel (not shown). A key lock on housing 26 of secure medication dispenser 12 may be provided for safety and theft. Further, housing 26 of secure medication dispenser 12 may have changeable bins to accommodate user's liking. Further, secure medication dispenser 12 may be equipped with detection mechanism for detecting a replenishment of plurality of medications. Outer surface of housing 26 of secure medication dispenser 12 may be designed using logos, design, color and the like. As based on timer 38, dosage is automatically released, thus secure medication dispenser 12 may be highly useful for users suffering from life threatening ailments. Further, secure medication dispenser 12 is locked and sealed in such a manner that only authorized user is allowed to access plurality of medications, but one at a time and at preset timings and dosages. In accordance with an embodiment, medication may be vertically ejected or at a defined angle, such as 60 degree, to be retrieved by hand, mouth, dog's claws, and the like. Secure medication dispenser 12 may be mounted anywhere with help of nylon strips or Velcro, or suction cups.

In accordance with an embodiment, color of housing of secure medication dispenser 12 may be any color, such as yellow, silver, and the like. All systems and buttons on housing are suitable labeled.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A secure medication dispenser, comprising:
   a housing including a top edge and a bottom edge, wherein said top edge is shorter than said bottom edge, said housing further including a first side edge and a second side edge being parallel to each other and extends upwardly from said bottom edge, said housing further including a first slanting edge and a second slanting edge each slanting inwardly and extending to meet said top edge, a rear plate pivotally mounted to said first slanting edge of said housing adapted to serve as a lid, a face plate abutting with said second slanting edge, said housing further including a handle extending from a sidewall of said housing, said rear plate further including a first loading point, a second loading point, and a third loading point each having a circular shape, wherein said housing comprises:
      a time to release a specified dosage of each of a plurality of medications;
      an environment control system configured to control one or more physical environmental characteristics for said plurality of medications inside said housing to preserve corresponding potencies;
      a plurality of authorization mechanisms located on said face plate of said housing, said face plate further including a first dispensing point and a second dispensing point having a circular shape; and
      a plurality of trays located within said housing adapted to hold the plurality of medications.

2. The secure medication dispenser of claim 1, wherein said environment control system comprises a humidifier to control humidity and temperature inside said housing.

3. The secure medication dispenser of claim 1, wherein said housing further includes suction cups configured to be mounted on bottom surface of said housing of said secure medication dispenser.

4. The secure medication dispenser of claim 1, wherein said face plate of said housing further comprises an LED light system configured to indicate low supply of one or more of said plurality of medications.

5. The secure medication dispenser of claim 1, wherein said housing further comprising a top plate adapted to be open and closed.

6. The secure medication dispenser of claim 1, wherein said plurality of medications comprise two or more of a cigarette, a cigar, a joint, an mm medication, and a blunt.

7. The secure medication dispenser of claim 1, wherein said one or more physical environmental characteristics correspond to a humidity level inside said housing.

8. The secure medication dispenser of claim 1, wherein said plurality of authorization mechanisms located on said face plate comprises two or more of a fingerprint recognition device and a voice recognition device.

9. The secure medication dispenser of claim 1, wherein a user is a patient suffering from Alzheimer, Dementia, Chronic pain, Epilepsy, Cognitive Dysfunction, Memory loss, or other such ailment.

10. A secure medication dispenser, consisting of:
    a) a housing including a top end and a bottom end, wherein said top end is shorter than said bottom end, wherein said housing further includes a first edge and a second edge being parallel to each other and extending upwardly from said bottom end, said housing further including a first slanting edge and a second slanting edge slanting inwardly and extending to meet said top end, wherein said first slanting edge includes a rear plate pivotally engaged with said first slanting edge and adapted to serve as a lid, wherein said second slanting edge includes a face plate abutting thereon, said housing further including a humidifier located therein, wherein said humidifier controls a level of humidity within said housing, said housing further including a sidewall having a handle extending thereout, wherein said handle includes a "U"-shaped configuration, said bottom end further including retractable suction cups mounted to a bottom surface of said housing;
    b) a plurality of receiving trays located within said housing which holds a plurality of medications, wherein said plurality of medications include a cigarette, a joint, and a cigar, wherein said housing further includes a storage area containing said plurality of receiving trays;
    c) a plurality of authorization mechanisms including a voice recognition system and a fingerprint recognition system located on said face plate, wherein said face plate further includes an LED light system, said face plate further including two dispensing points each having a circular shape, said face plate further including a timer adapted to set a time to release a specified dosage of said plurality of medications;

d) a first loading point, a second loading point, and a third loading point located on said rear plate of said housing, wherein said first loading point, said second loading point, and said third loading point each have a corresponding top button and a corresponding bottom button; and e) a top plate located on said top end of said housing, wherein in said plurality of medications is dispensed through said top plate in a slanting direction.

* * * * *